United States Patent [19]

Berlin

[11] Patent Number: 5,795,310

[45] Date of Patent: Aug. 18, 1998

[54] MODULAR WORK EVALUATION APPARATUS

[76] Inventor: Stanley Berlin, 4 Stream Ct., Owings Mills, Md. 21117

[21] Appl. No.: 729,882

[22] Filed: Oct. 15, 1996

[51] Int. Cl.⁶ ........................................ A61B 5/00
[52] U.S. Cl. ...................................... 600/595
[58] Field of Search .................. 600/587, 595; 33/512; 482/139, 904, 45; 434/260; 73/379.01

[56] References Cited

U.S. PATENT DOCUMENTS

| | | | |
|---|---|---|---|
| 4,471,957 | 9/1984 | Engalitcheff, Jr. | 272/132 |
| 4,742,832 | 5/1988 | Kauffmann et al. | 600/595 |
| 5,251,644 | 10/1993 | Fitzgerald | 600/595 |
| 5,454,773 | 10/1995 | Blanchard et al. | 482/133 |
| 5,490,517 | 2/1996 | Whitman et al. | 600/595 |
| 5,645,078 | 7/1997 | Marmer et al. | 600/595 |

*Primary Examiner*—Max Hindenbury
*Assistant Examiner*—Charles Marmor, II
*Attorney, Agent, or Firm*—Royal W. Craig

[57] ABSTRACT

A modular universal work evaluation apparatus to give therapists the ability to measure job task performance in the context of a variety of specific jobs or tasks. The invention generally comprises a main bench unit forming a walled semi-enclosure with a removable top, one or more simulated work evaluation stations enclosed within the main bench unit, and one or more work evaluation stations attachable to the main bench unit. All simulated work evaluation stations include a plurality of workable components for simulating specific job related tasks performed by the patient at work. The internal work evaluation stations include one or both of a simulated shoveling pit and/or a simulated engine block accessible by removing the removable top. The external work evaluation stations include one or more of a shelving unit for determining how much weight a patient can lift at various heights, a mechanical fastener module with a plurality of fasteners that can be assembled and disassembled with conventional tools, a simulated plumbing module having a plurality of valves and pipes that can be worked with conventional plumber's tools, and a simulated electrical module having various electrical components that can be worked with conventional electrician's tools.

22 Claims, 7 Drawing Sheets

MODULAR WORK EVALUATION APPARATUS

BACKGROUND OF THE INVENTION

1. Field of the Invention

The present invention relates to work evaluation in which therapists measure job task performance of patients after job-related injuries and, more particularly, to a modular work evaluation apparatus with integral work evaluation stations including (but not limited to) a gravel pit to assess shoveling, a shelving unit to determine how much weight can be lifted at various heights, a mechanical fastener module to assess assembly/disassembly skills, an engine block module, a plumbing module, and an electrical module for assessment of manual dexterity during disassembly and repair.

2. Description of the Background

Therapists are often called upon to assess the degree of impairment of job-related functions (and the subsequent degree of rehabilitation) after a patient has incurred a job-related injury.

A variety of generic muscle testing methods and devices have been proposed in the prior art. The most basic entail/require patients to push, pull, or exert some other force on their examining physician. The physician endeavors to recall his impression of the forces which the patient was able to exert during a previous visit, and this is compared over time to reach a conclusion regarding the patient's condition. The consistency and reliability of such impressions and evaluation procedures is highly questionable. This is particularly true where a physician sees hundreds of patients between visits.

More reliable muscular evaluation devices have been proposed for use in testing muscles or muscle groups at substantially any position over the patient's body. These generally comprise specialized resistance devices adapted for use in testing muscular force. For example, U.S. Pat. No. 4,939,933 to Curran shows an isometric strength-testing method and device using an adjustable testing station and a variety of attachments. U.S. Pat. No. 3,752,144 to Weigle, Jr. shows a muscular evaluation device including multiple stations at which a force sensor is placed against parts of a user's body to record strength. However, these and like devices fail to allow evaluation of job-related functioning in the specific context of the patient's actual job. Consequently, such devices have not been found to be practical or widely acceptable for use in job-related evaluation.

There are a number of more job-specific devices. For instance, U.S. Pat. No. 5,498,162 to Schaefer shows a method for demonstrating a lifting technique using a box containing weights. U.S. Pat. No. 3,973,332 to Slomski shows a device for evaluating the psycho-physiological response of a driver. U.S. Pat. No. 4,471,957 to Engalitcheff, Jr. shows a method and work-bench device for rehabilitating damaged limbs for use in operating familiar hand-tools. The device employs resistance training on a rotatable shaft. U.S. Pat. No. 5,211,562 to Wickstrom discloses a method and device for evaluating physical ability with ordinary mechanics tools. Also, U.S. Pat. No. 5,498,162 to Schaefer shows a method for demonstrating a lifting technique using a box containing weights. While the above devices are more job-specific, and therefore allow evaluation in the context of only one job-related task. As such, they are not practical or widely acceptable for use in universal job-related evaluation. Presently, no known work evaluation device exists whereby a therapist can reliably and consistently evaluate the function of a patient suffering from a muscle disorder in the specific context of a range of particular jobs. It would be greatly advantageous to provide a more universal work evaluation device.

SUMMARY OF THE INVENTION

In accordance with the above, it is an object of the present invention to provide a work evaluation apparatus to assess various job related functions of patients after injury at work, and in the specific context of their normal job tasks.

It is another object to provide a compact modular work evaluation apparatus with a variety of integral and easily-accessible work evaluation stations.

It is another object to provide a modular work evaluation apparatus with a variety of work evaluation stations corresponding to job-tasks in which job-related injury is most prevalent.

It is still another object to provide a modular work evaluation apparatus which allows for easy and convenient retrofit inclusion of additional work evaluation stations as the need arises.

According to the present invention, the above-described and other objects are accomplished by providing a modular universal work evaluation apparatus to give therapists the ability to measure job task performance in the context of a variety of specific jobs or tasks. The invention generally comprises a main bench unit forming a walled semi-enclosure with a removable top, at least one simulated work evaluation station enclosed within the main bench unit, and at least one work evaluation station attachable to the main bench unit. All simulated work evaluation stations include a plurality of workable components for simulating specific job related tasks performed by said patient at work. The internal work evaluation stations include one or both of a simulated shoveling pit and/or a simulated engine block accessible by removing the removable top.

The simulated shoveling pit includes a substance to be shoveled (such as gravel), and an inclined shelf supported within the main bench unit. The inclined shelf is spaced from and angled downward toward the back wall of the main bench unit to allow the substance (when shoveled from a floor of the main bench unit onto the shelf) to recirculate back to said floor for further shoveling.

The simulated engine block further comprises a shelf attached interiorly to a wall of the main bench unit, and a plurality of threaded sockets and corresponding spark plugs and an oil filter which can be installed and removed to/from the sockets with conventional mechanic's tools.

The external work evaluation stations include one or more of 1) a shelving unit for determining how much weight a patient can lift at various heights; 2) a mechanical fastener module with a plurality of fasteners that can be assembled and disassembled with conventional tools; 3) a simulated plumbing module having a plurality of valves and pipes that can be worked with conventional plumber's tools; and 4) a simulated electrical module having various electrical components that can be worked with conventional electrician's tools.

The shelving unit includes an adjustable-height shelf and adjustable-weight container positional on the shelf for determining how much weight a patient can lift at various heights.

The mechanical fastener module includes a vertical pole with a plurality of pre-drilled holes there through and fasteners for attachment through the holes which can be assembled and disassembled. The pre-drilled holes are preferably spaced along said pole at various heights and angles to prompt the patient to assemble and disassemble the fasteners while assuming various body positions.

The simulated plumbing module includes a vertical panel attachable to an exterior wall of the main bench, a horizontal shelf attached to and extending outward from the vertical panel, and a plurality of plumbing components including a faucet mounted on the horizontal shelf, and a plurality of valves and pipes mounted beneath the horizontal shelf.

The simulated electrical module includes a vertical panel attachable to an exterior wall of the main bench, and various electrical components mounted on the vertical panel.

Of course, many modifications of the invention would be apparent to those skilled in the art. Specifically, further simulated work evaluation modules may be added to the basic apparatus as the need arises. Such modifications are considered within the spirit and scope of the invention.

BRIEF DESCRIPTION OF THE DRAWINGS

Other objects, features, and advantages of the present invention will become more apparent from the following detailed description of preferred embodiments and certain modifications thereof when taken together with the accompanying drawings in which.

DETAILED DESCRIPTION OF THE PREFERRED EMBODIMENTS

The present invention is a universal work evaluation apparatus to give therapists the ability to measure the specific job task performance of patients after job-related injuries, and across a range of common job tasks. The work evaluation apparatus is designed to be as compact as possible to minimize space, yet fully functional to addressing a wide range of specific job tasks. This is accomplished by a modular design that incorporates a variety of integral and easily-accessible work evaluation stations. Presently, the work evaluation apparatus is configured to provide modular work stations corresponding to specific job-tasks in which job-related injury is most prevalent. However, the work evaluation apparatus is designed to allow easy and convenient retrofit inclusion of additional work evaluation stations as the need arises.

Figure 1:
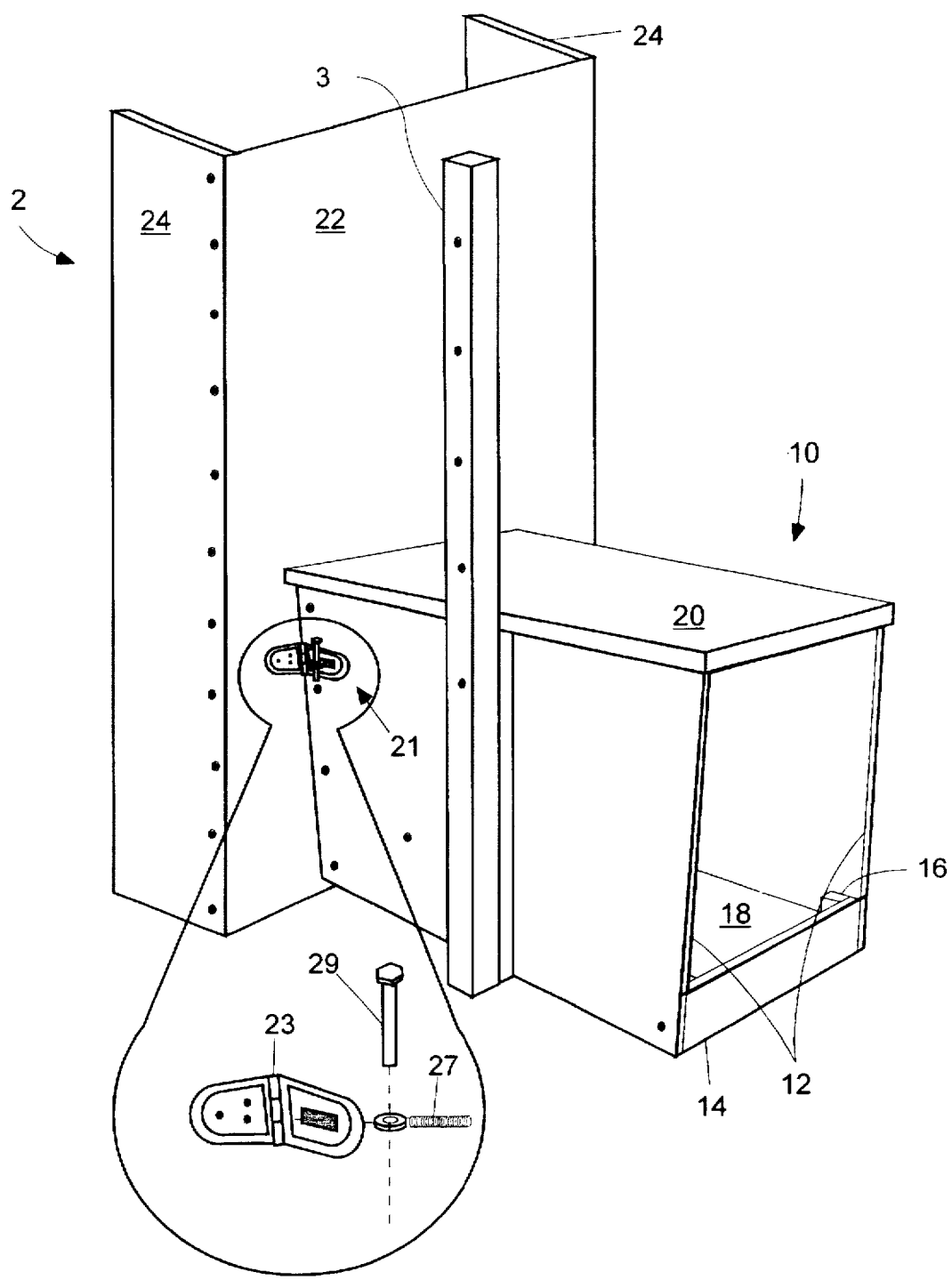
FIG. 1 is a side perspective view of a modular work evaluation apparatus 1 according to one embodiment of the present invention.

FIG. 1 is a side perspective view of a modular work evaluation apparatus 1 according to one embodiment of the present invention. The illustrated work evaluation apparatus 1 generally includes a main bench unit 10 with lift-off cover 20, a shelving unit 2 for assessment of a patient's lifting capability at various heights, and a mechanical fastener module 3 for assessment of a patient's manual dexterity when manipulating wrenches and other hand tools. Other modules (to be described) are enclosed within the main bench unit 10 or are attached to its exterior for assessing a variety of other job-specific tasks. In its present and illustrated form the work evaluation apparatus 1 including main bench unit 10, shelving unit 2, mechanical fastener module 3, and all other modules are constructed substantially of hardwood panels with hardwood reinforcements and secured by conventional means such as bolts and tee nuts and/or wood screws or the like. However, it should be understood that plastic, fiberglass, or metal panels secured by appropriate means will serve the same purpose and such is a matter of design choice.

In the illustrated hardwood embodiment, the main bench unit 10 is enclosed on three sides by three upright side panels 12. A floor panel 18 underlies and is secured to all three side panels 12, and a removable top panel 20 serves as a top enclosure and work surface.

The outwardly facing side is substantially unbounded, but is provided with a lateral brace 14 connecting the floor panel 18 and opposing side panels 12. Corner reinforcing blocks 16 are secured at the lower four corners of the main bench unit 10 to reinforce the structure. All wood panels, blocks and struts are bolted or screwed together by conventional bolts and tee nuts and/or wood screws.

The removable top panel 20 is unsecured but is preferably held in place atop the side panels 12 by downwardly protruding ribs or pegs (not shown) which conform to the opening.

The dimensions of the main bench unit 10 and all other modules (to be described) are significant insofar as they are designed to accurately reflect the characteristics of actual occupational simulations within the constraints of a very compact overall unit. Accordingly, suggested dimensions will be provided. However, the exact dimensions are a matter of design choice and may be varied to fit particular needs. The suggested dimensions are therefore exemplary and reasonable variations are considered to be within the spirit and scope of the present invention.

Suggested dimensions of the main bench unit 10 are as follows:
Height: 32½"
Length: 48"
Width: 28½"

The shelving unit 2 is a three-walled enclosure including two opposing side panels 24 secured to a back panel 22. The back panel 22 of shelving unit 2 is attached to the main bench unit 10 as shown by a pair of hasp assemblies 21 (detailed in enlarge bubble illustration) secured to opposing sides of the main bench unit 10. Each hasp assembly 21 includes a hinged hasp 23 secured at one end to the back panel 22 of the shelving unit 2. The free end of each hasp 23 is defined by a slot which can be pivoted into position over a yoked bolt 27, bolt 27 being secured in the side wall 12 of main bench unit 10. A conventional bolt 29 is inserted downward through the yoke of bolt 27 and is anchored therein by a conventional tee nut to thereby secure shelving unit 2 to the main bench unit 10.

The two opposing side panels 24 and back panel 22 of shelving unit 2 are of equal vertical dimensions and stand approximately six (6) feet to allow comprehensive assessment of lifting capability over a patient's normal lifting range.

A mechanical fastener module 3 (to be described more fully) is secured to one side of the main bench unit 10 to allow convenient assessment of a patient's manual dexterity while manipulating standard wrenches, screw drivers and other hand tools. The mechanical fastener module 3 includes an upright pole spaced from shelving unit 2 and a variety of attached fasteners to allow comprehensive assessment of manual dexterity over a patient's normal vertical range.

Figure 2:
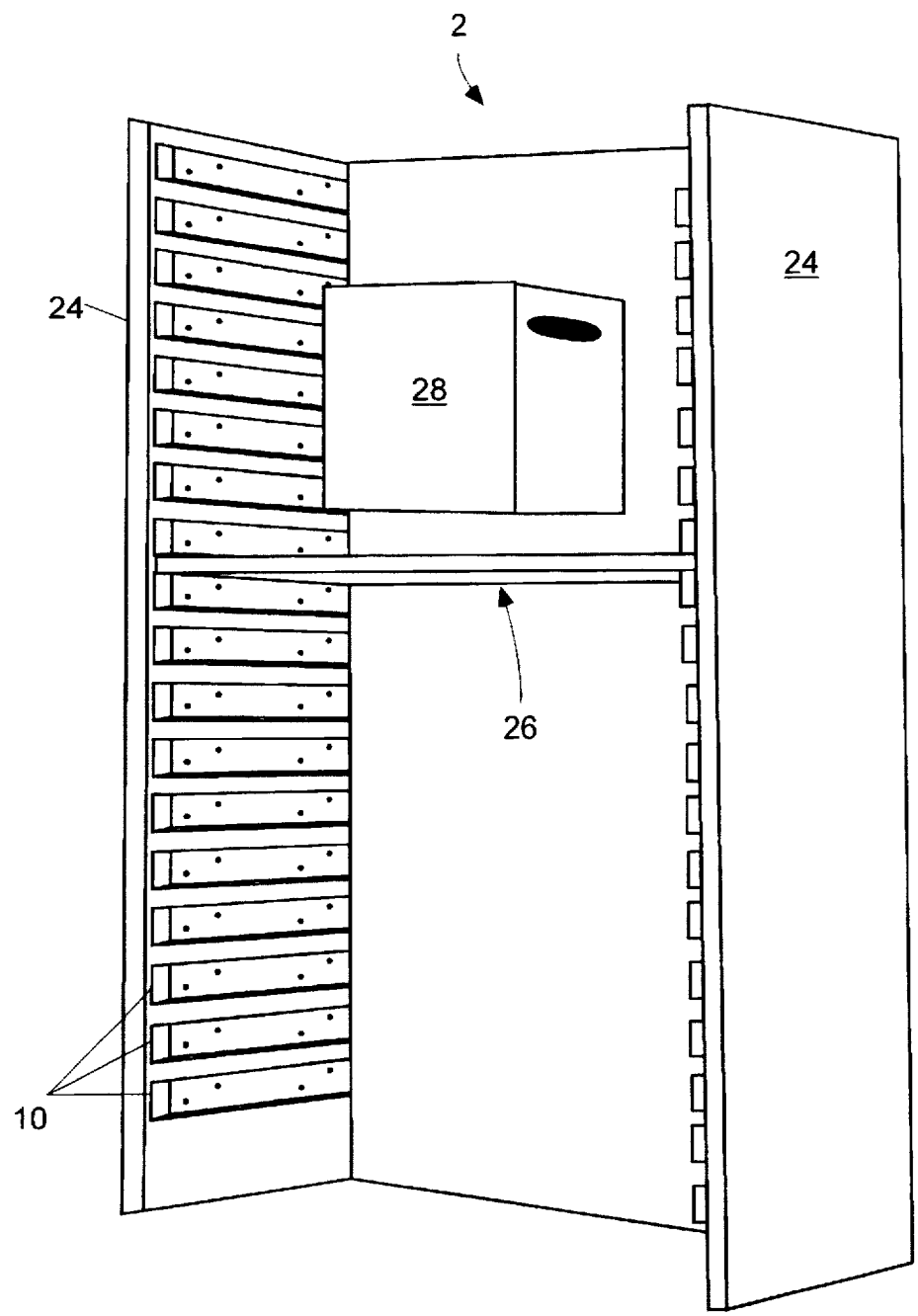
FIG. 2 is a front perspective drawing of a shelving unit 2 as used in the modular work evaluation apparatus 1 of FIG. 1.

FIG. 2 is a front perspective drawing of the shelving unit 2 as used in the modular work evaluation apparatus 1 of FIG. 1. Shelving unit 2 includes an adjustable shelf 26 to allow the therapist to determine how much weight can be lifted by a patient at various heights. The lateral extent of the adjustable shelf 26 conforms to the spacing between side panels 24. The specific height of shelf 26 is set by seating shelf 26 within opposing slots formed between equally spaced supporting slats 27 attached to both side panels 24. An equal number of slats 27 are secured by conventional wood screws or bolts along the inner surface of both side panels 24 to allow the therapist to select any height ranging from approximately one to six feet. Once the shelf 26 is inserted at an appropriate height, a box 28 containing a predetermined weight is set in front on the floor. Box 28 is formed with slots in the sides which serve as handles. A patient may grasp the weighted box 28 by its side-handles and attempt to lift it and place it atop the shelf 26, thereby exhibiting their lifting capability for the therapist. The weight of the box 28 and height of the shelf 26 are variables which serve to indicate the lifting strength of the patient.

Suggested dimensions of the shelving unit 2 are as follows:
Height: 72"
Length: 37"
Width: 16"

Figure 3:
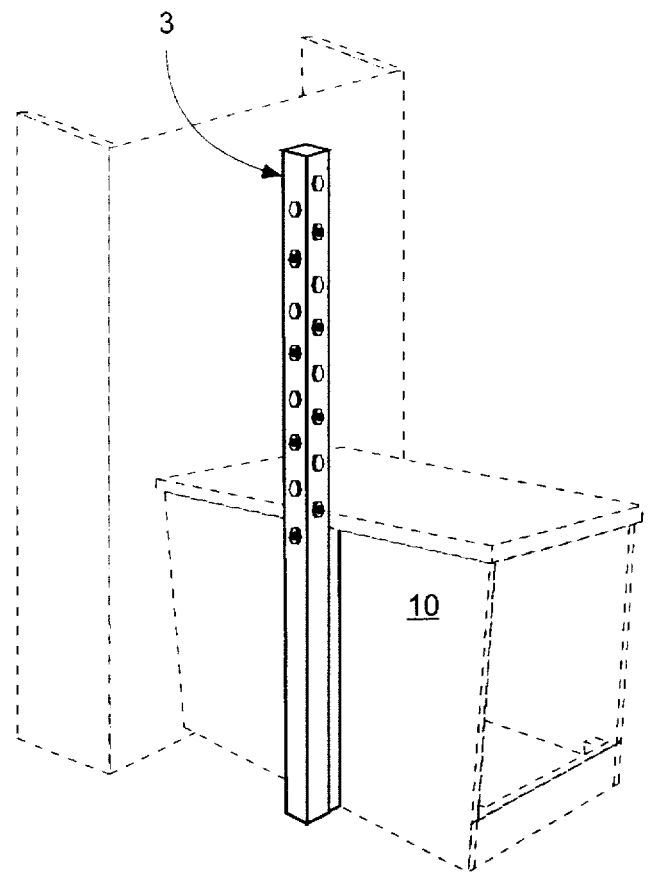
FIG. 3 is a side perspective view of a mechanical fastener module 3 as used in the modular work evaluation apparatus 1 of FIG. 1.

FIG. 3 is a side perspective view of the mechanical fastener module 3 as used in the modular work evaluation apparatus 1 of FIG. 1. The mechanical fastener module 3 comprises vertical pole 3 of square cross-section with an assortment of nuts, washers and bolts attached along its length, the latter of which can be disassembled and assembled with conventional wrenches or other hand tools. This allows a therapist to measure the manual dexterity of the patient in the context of assembling and/or disassembling. Preferably the assortment of nuts, washers and bolts includes an array of conventional hex bolts, flathead screws and hex screws to allow testing of dexterity with corresponding wrenches and screwdrivers. The assortment of nuts, washers and bolts are evenly spaced and inserted in the pole 3 at regular intervals within pre-drilled holes.

There are several optional simulation modules which can be stored within the confines of the main bench unit 10 and removed as desired and attached thereto for other types of evaluation.

Figure 4:
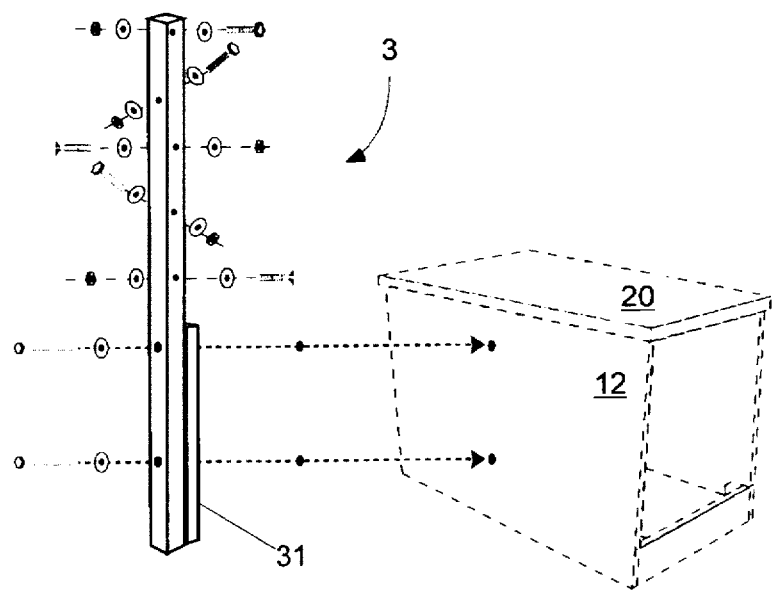
FIG. 4 is a break-away perspective view of the mechanical fastener module 3 of FIG. 3.

FIG. 4 is an exploded perspective view of the mechanical fastener module 3 of FIG. 3. An integral spacer 31 is permanently attached to a pole 3 to allow the pole 3 to extend unobstructed past the top cover 20. Pole 3 (and spacer 31) are secured to one side panel 10 of the main bench unit 10 via conventional bolts and tee nuts (presently ⅛" bolts and mating tee nuts), the bolts protruding through both pole 3 and spacer 31 into side panel 12 of the main bench unit 10. The mechanical fastener module 3 may be conveniently attached/removed by means of a ⅛" wrench supplied with the unit.

It is preferred that the assortment of nuts, washers and bolts be inserted through all four sides of pole 3 to insure that the patient must deal with various angles and postures. Similarly, it is preferred that the nuts, washers and bolts be inserted along both the upper length of pole 3 and the lower length of pole 3 to insure that the patient can be evaluated in both standing and crouching positions.

Figure 5:
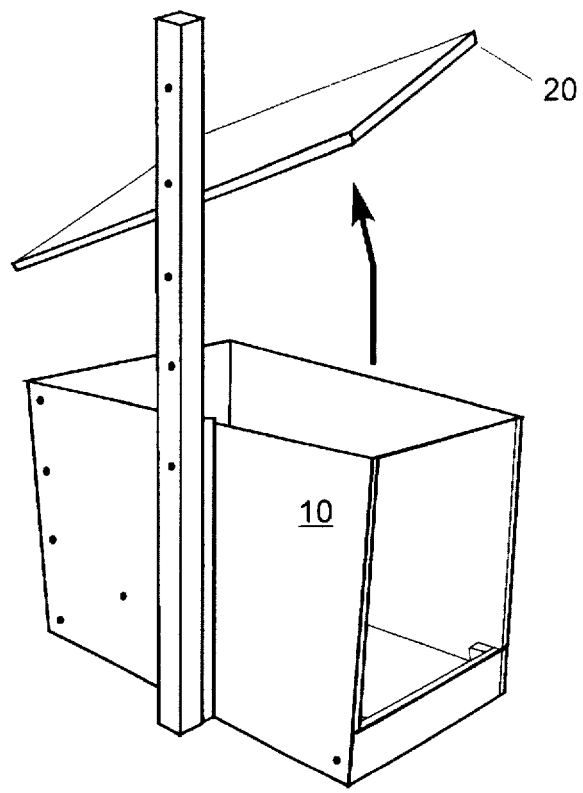
FIG. 5 is a side perspective view illustrating removal of the apparatus cover 20 to gain access to the engine block module 4 and gravel pit module 5.

FIG. 5 is a side perspective view illustrating removal of the main bench unit top cover 20 to gain access to the engine block module 4 and gravel pit module 5. Once the top cover 20 is removed, the interior of the main bench unit 10 is frontally exposed to give access to interior work evaluation modules to be described. One such interior work evaluation module is an engine block module.

Figure 6:
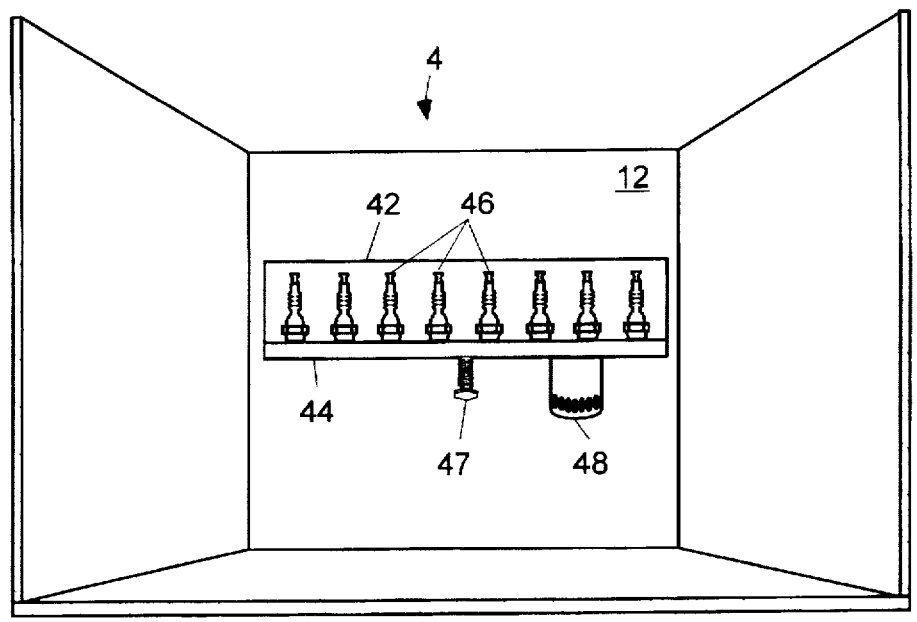
FIG. 6 is a front view of the engine block module 4.

FIG. 6 is a front view of the engine block module 4 which is secured to the rear side panel 12 of the main bench unit 10. The engine block module 4 comprises a vertical mounting board 42 secured by conventional bolts and tee nuts (presently ⅛" bolts and mating tee nuts) to the rear side panel 12 of main bench unit 10. The engine block module 4 may be conveniently attached/removed by means of a ⅛" wrench supplied with the unit. Vertical mounting board 42 supports an attached horizontal shelf 44 protruding approximately six inches toward the main bench unit 10 enclosure. A number of threaded metal sockets (not shown) are embedded in the horizontal shelf 44 and are adapted for screw-insertion of a corresponding number of conventional spark plugs 46. Similarly, a threaded metal bolt 47 is embedded beneath the horizontal shelf 44 and is adapted for screw-insertion of a conventional oil filter 48.

The array of upwardly mounted spark plugs 46 on shelf 44 and downwardly mounted oil filter 48 within the tight confines of the main bench unit 10 provide an extremely realistic simulation of an actual vehicle engine compartment. This insures that the attending therapist can acquire a practical evaluation of the ability of an injured mechanic to install and/or remove actual spark plugs and oil filters in their customary working environment. It is envisioned that further engine components may be added as desired such as air filters and housings, thermostats, etc. All mounted components can be taken apart and put back together with conventional mechanic's tools to be provided.

Suggested dimensions of the engine block module 4 are as follows:
Height (of vertical mounting board 42): 4"
Length (of vertical mounting board 42): 17"
Width (of vertical mounting board 42): 6½"

Figure 7:
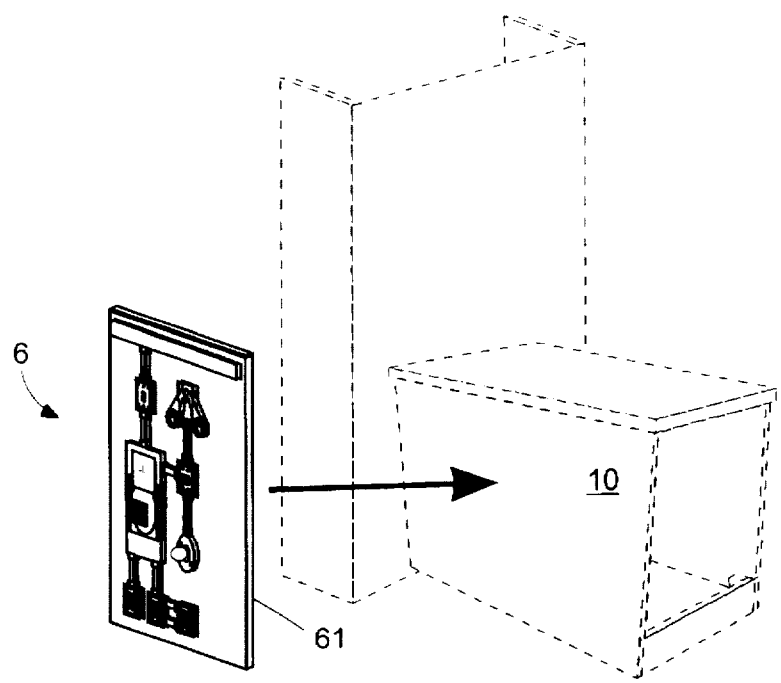
FIG. 7 is a side perspective view of the electrical module 6 illustrating its attachment to the main bench 10.

FIG. 7 is a side perspective view of the electrical module 6 illustrating its attachment to the main bench 10. Electrical module 6 includes various electrical components for assessment of manual dexterity during disassembly and repair of such devices. The components of electrical module 6 are secured to the face of a hardwood panel 61 that is in turn secured to one side panel 12 of the main bench unit 10. As before, one or more hardwood brackets (see ref 31 of FIG. 4) may be employed to serve as spacers thereby insuring that the electrical module 6 may extend unobstructed past the top cover 20. Panel 61 is secured by conventional bolts and tee nuts as shown (presently ⅛" bolts and mating tee nuts) which protrude into side panel 10 of the main bench unit 10. The electrical module 6 may be conveniently attached/removed by means of a ⅛" wrench supplied with the unit.

Suggested dimensions of the electrical module 6 are as follows:
Height (hardwood panel 61): 48"
Length (hardwood panel 61): 26"

Figure 8:
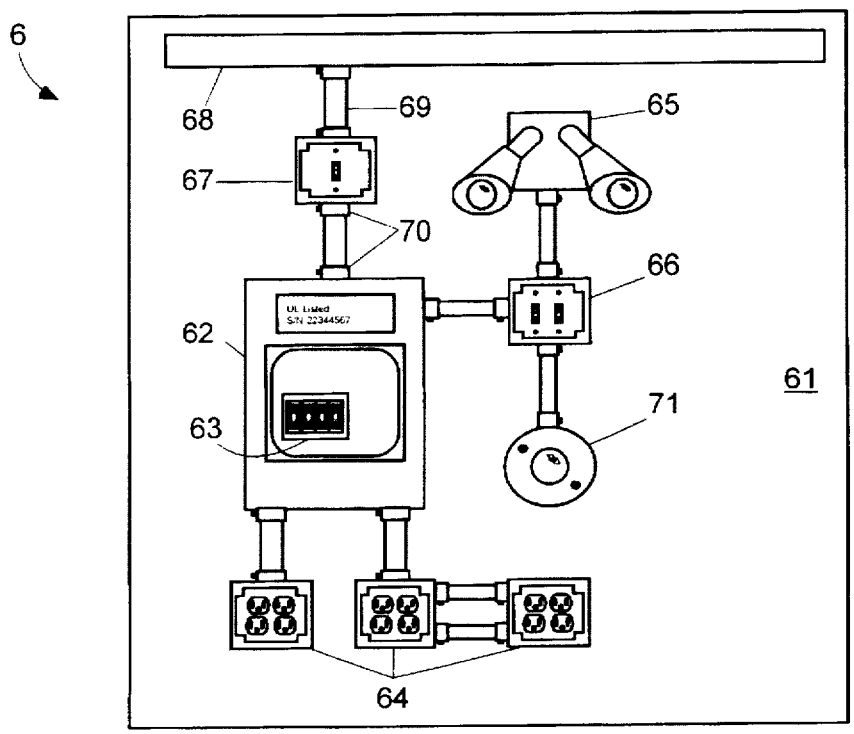
FIG. 8 is a front close-up view of the electrical module 6 of FIG. 7.

FIG. 8 is a front close-up view of the electrical module 6 of FIG. 7 illustrating a presently preferred array of standard electrical components. The illustrated components include a main junction box 62 with integral bank of circuit breakers 63. The main junction box 62 is electrically connected to other components by conduits 69 which are anchored by compression collars 70. The main junction box 62 is fed through a single-pole switch box 67 by a main power conduit 68. The main junction box 62 feeds three conventional quad-socket power outlet boxes 64, as well as a double-pole switch box 66. The double pole switch box 66 is connected to a dual overhead light 65 as well as a single-bulb light socket 71. All internal wiring is present. This particular array of electrical components insures that the attending therapist can acquire a practical evaluation of the ability of an injured electrician to install, remove and/or test actual wiring in their customary working environment. It is envisioned that further components may be added as desired, and all mounted components can be taken apart and put back together with conventional electrician's tools to be provided.

Figure 9:
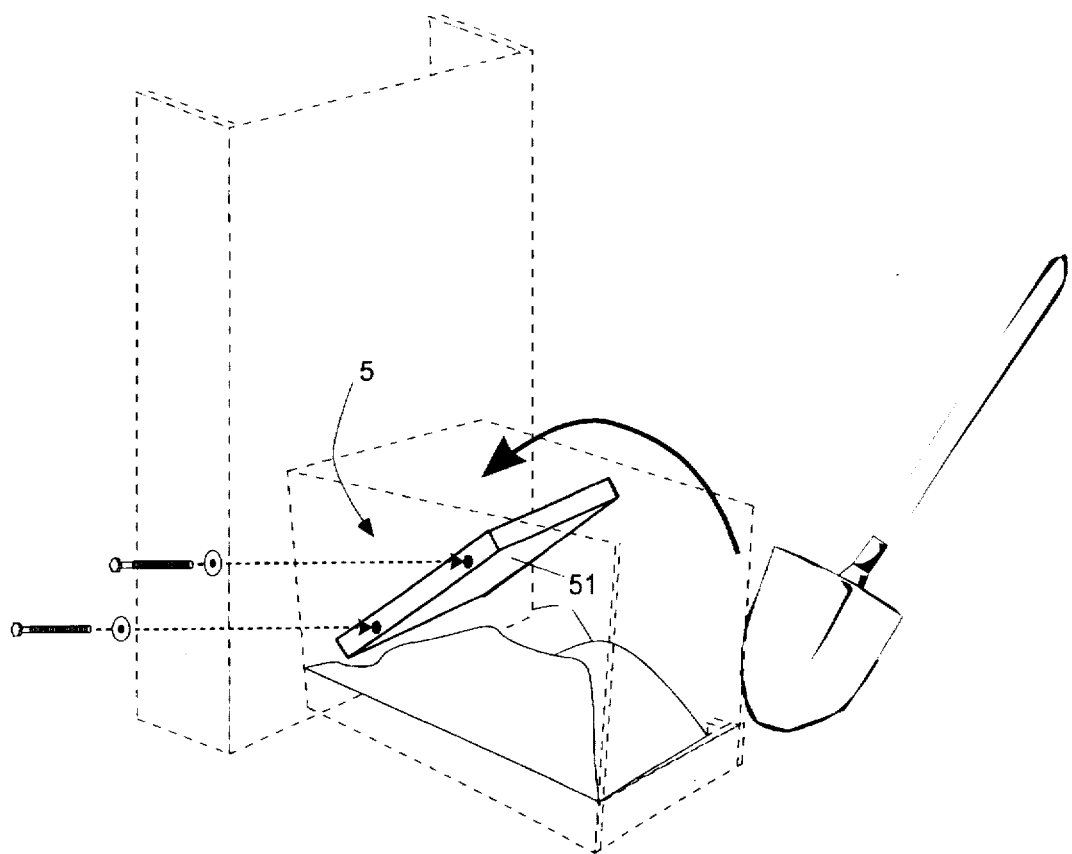
FIG. 9 is a side perspective view of the gravel pit module 5.

FIG. 9 is a side perspective view of the gravel pit module 5. The engine block module 4 should be removed prior to using the gravel pit module 5. Then, gravel or another substance is added to the interior confines of the main bench unit 10 and a standard shovel is employed to evaluate the ability of a laborer as they shovel gravel. In addition to the gravel itself, the gravel pit module 5 primarily comprises an inclined shelf 51 which is attached by conventional bolts and tee nuts (with washers) to both opposing side panels 12 of the main bench unit. Inclined shelf 51 is attached so to span the interior of the main bench unit 10 between opposing side panels 12. The incline of shelf 51 is calculated to allow gravel shoveled onto its upper surface to run off, and the bottom edge of inclined shelf 51 is spaced a short distance from the rear panel 12 of main bench unit 10 to provide a clearance for the gravel to escape downward and back onto the floor panel 18 of the main bench unit 10. In this configuration, gravel is recirculated and can be continuously shoveled to give the attending therapist a practical evaluation of the ability of an injured laborer to shovel in their customary working environment for a prolonged period of time. It is envisioned that other substances may be used together with their appropriate implements.

Figure 10:
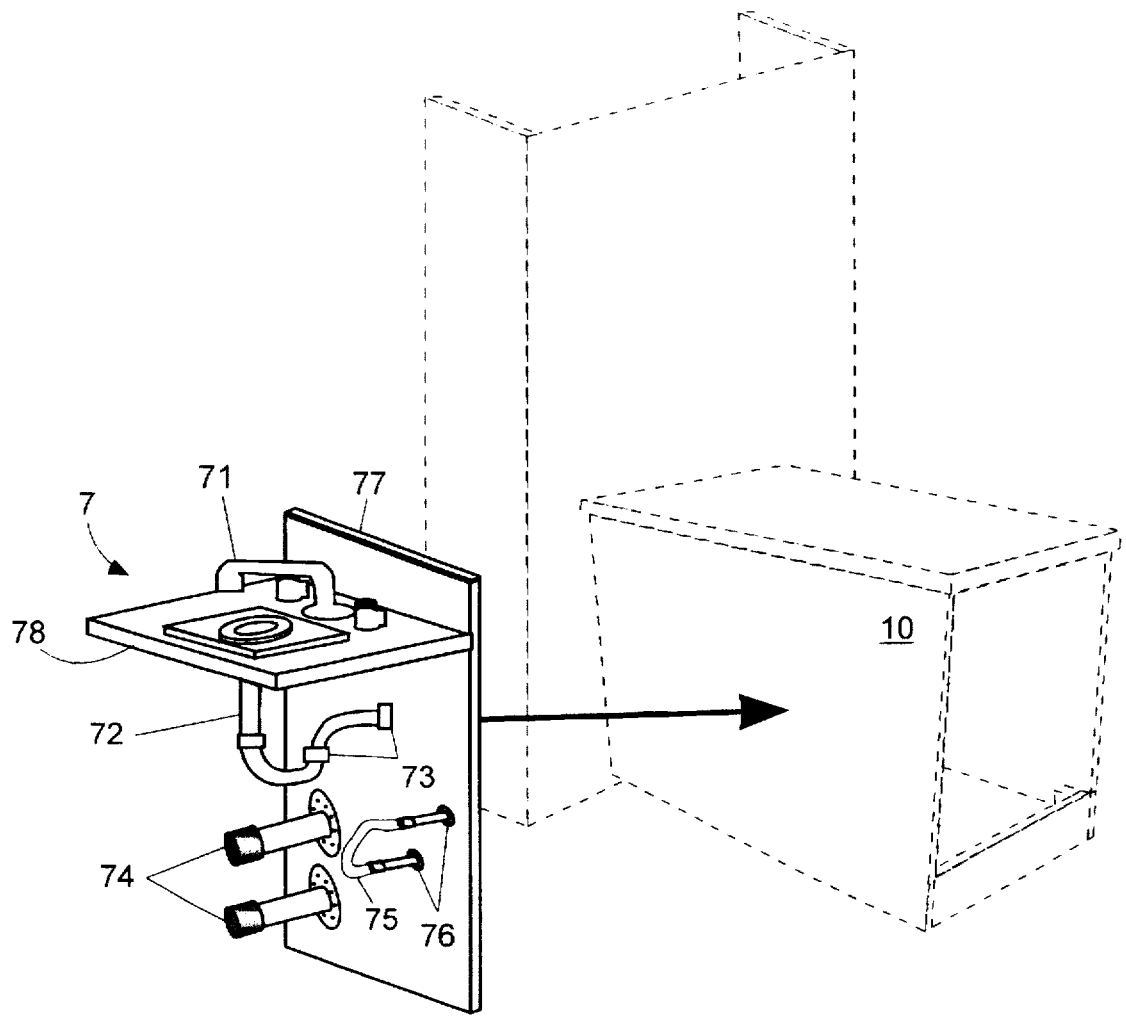
FIG. 10 is a side perspective view of the plumbing module 7 illustrating its attachment to the main bench 10.

FIG. 10 is a side perspective view of the plumbing module 7 illustrating its attachment to the main bench 10. The components of plumbing module 7 are secured to a horizontal shelf 78 and to the face of an attached vertical hardwood panel 77. The vertical panel 77 is in turn secured to one side panel 10 of the main bench unit 10. As before, one or more hardwood brackets (see ref 31 of FIG. 4) may be integrally attached to serve as spacers thereby insuring that the plumbing module 7 may extend unobstructed past the top cover 20. Vertical panel 77 is secured by conventional bolts and tee nuts (presently ⅜" bolts and mating tee nuts) which protrude into side panel 10 of the main bench unit 10. The plumbing module 7 may be conveniently attached/removed by means of a ⅜" wrench supplied with the unit.

Suggested dimensions of the plumbing module 7 are as follows:
Height (vertical hardwood panel 77): 31"
Length (vertical hardwood panel 77): 21"

Plumbing module 7 is shown to include a presently preferred array of standard plumbing components which can be assembled and put back together with conventional plumber's tools. The illustrated components include a sink fixture with faucet 71 and a drain extending downward to a conventional U-trap formed of conduits 72 coupled by compression fittings 73. Two capped main conduit sections 74 are attached and extend forwardly from the vertical panel 77. Likewise, two smaller conduit sections 76 are attached and extend forwardly from the vertical panel 77, the two being connected by a length of flexible tubing 75. All fluid connections and the particular chosen array of plumbing components insures that the attending therapist can acquire a practical evaluation of the ability of an injured plumber to install, remove and/or test actual plumbing assemblies of various sizes while in their customary working environment (e.g., within tight confines in a crouched position under a sink. It is envisioned that further plumbing components may be added as desired, and all mounted components can be taken apart and put back together with conventional plumber's tools to be provided.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that within the scope of the appended claims, the invention may be practiced otherwise than as specifically set forth herein.

I claim:

1. A work evaluation apparatus for assessing job related functions of a patient after injury at work, comprising:
   a main bench unit forming a walled semi-enclosure with removable top;
   a first work evaluation station enclosed within said main bench unit;
   a second work evaluation station attachable to said main bench unit;
   whereby said work evaluation stations include a plurality of workable components for simulating specific job related tasks performed by said patient at work.

2. The work evaluation apparatus for assessing job related functions according to claim 1, wherein said first work evaluation station further comprises a simulated shoveling pit that is accessed by removing said removable top.

3. The work evaluation apparatus for assessing job related functions according to claim 2, wherein said simulated shoveling pit further comprises a substance to be shoveled, and an inclined shelf supported within said main bench unit, said inclined shelf being spaced from and angled downward toward a wall of said main bench unit to allow the substance when shoveled from a floor of said main bench unit onto said shelf to recirculate back to said floor for further shoveling.

4. The work evaluation apparatus for assessing job related functions according to claim 3, wherein said inclined shelf is attached between two side walls of said main bench unit and is spaced from and angled downward toward an end wall thereof.

5. The work evaluation apparatus for assessing job related functions according to claim 1, wherein said first work evaluation station further comprises a simulated engine block that is accessed by removing said removable top.

6. The work evaluation apparatus for assessing job related functions according to claim 5, wherein said simulated engine block further comprises a shelf attached to interiorly to a wall of said main bench unit, and a plurality of threaded sockets and corresponding spark plugs and an oil filter which can be installed and removed to/from said sockets with conventional mechanic's tools.

7. The work evaluation apparatus for assessing job related functions according to claim 1, wherein said second work evaluation station further comprises a shelving unit attached exteriorly of said main bench unit, said shelving unit including an adjustable-height shelf and adjustable-weight container positional on said shelf for determining how much weight said patient can lift at various heights.

8. The work evaluation apparatus for assessing job related functions according to claim 7, wherein said shelving unit further comprises a walled semi-enclosure having opposing side-walls, and a plurality of opposing horizontal slats spaced along and attached to the interior of said side-walls for supporting said adjustable-height shelf at a selectable height.

9. The work evaluation apparatus for assessing job related functions according to claim 8, wherein said shelving unit is removably attached exteriorly to said main bench unit by a pair of hasp assemblies.

10. The work evaluation apparatus for assessing job related functions according to claim 9, wherein each one of said pair of hasp assemblies includes a hinged hasp secured at one end to a back panel of the shelving unit and having a free end defined by a slot, and a yoked bolt secured in a side wall of main bench unit, the slotted free end of the hinged hasp being pivotable over the yoke of said bolt, whereby the free end of the hinged hasp may be anchored to the yoked bolt by inserting a pin through the yoke of said bolt to thereby secure the shelving unit to the main bench unit.

11. The work evaluation apparatus for assessing job related functions according to claim 1, wherein said second work evaluation station further comprises a mechanical fastener module including a vertical pole having a plurality of pre-drilled holes therethrough and fasteners for attachment through said holes which can be assembled and disassembled with conventional tools.

12. The work evaluation apparatus for assessing job related functions according to claim 11, wherein said pre-drilled holes are spaced along said pole at various heights and angles to prompt said patient to assemble and disassemble said fasteners in various body positions.

13. The work evaluation apparatus for assessing job related functions according to claim 1, wherein said second work evaluation station further comprises a simulated plumbing module including a vertical panel attachable to an exterior wall of said main bench, a horizontal shelf attached to and extending outward from said vertical panel, and a plurality of plumbing components including a faucet mounted on said horizontal shelf, and a plurality of valves and pipes mounted beneath said horizontal shelf which can be worked with conventional plumber's tools.

14. The work evaluation apparatus for assessing job related functions according to claim 1, wherein said second work evaluation station further comprises a simulated electrical module including a vertical panel attachable to an exterior wall of said main bench, and various electrical components mounted on said vertical panel which can be worked with conventional electrician's tools.

15. A work evaluation apparatus for assessing job related functions of a patient after injury at work, comprising:

a main bench unit forming a walled semi-enclosure with removable top;

a simulated shoveling pit enclosed within said main bench unit and accessible by removing said removable top;

a simulated engine block enclosed within said main bench unit and accessible by removing said removable top;

a shelving unit attached exteriorly of said main bench unit, said shelving unit including an adjustable-height shelf and adjustable-weight container positional on said shelf for determining how much weight said patient can lift at various heights;

a mechanical fastener module attached exteriorly of said main bench unit, said mechanical fastener module including a vertical pole having a plurality of pre-drilled holes there through and fasteners for attachment through said holes which can be assembled and disassembled with conventional tools;

a simulated plumbing module attached exteriorly of said main bench unit, plumbing module including a plurality of plumbing components that can be worked with conventional plumber's tools; and a simulated electrical module attached exteriorly of said main bench unit, said electrical module including a plurality of electrical components that can be worked with conventional electrician's tools; whereby said work evaluation stations simulate respective specific job related tasks performed by said patient at work.

16. The work evaluation apparatus for assessing job related functions according to claim 15, wherein said simulated shoveling pit further comprises a substance to be shoveled, and an inclined shelf supported within said main bench unit, said inclined shelf being spaced from and angled downward toward a wall of said main bench unit to allow the substance when shoveled from a floor of said main bench unit onto said shelf to recirculate back to said floor for further shoveling.

17. The work evaluation apparatus for assessing job related functions according to claim 16, wherein said inclined shelf is attached between two side walls of said main bench unit and is spaced from and angled downward toward an end wall thereof.

18. The work evaluation apparatus for assessing job related functions according to claim 15, wherein said simulated engine block further comprises a shelf attached to interiorly to a wall of said main bench unit, and a plurality of threaded sockets and corresponding spark plugs and an oil filter which can be installed and removed to/from said sockets with conventional mechanic's tools.

19. The work evaluation apparatus for assessing job related functions according to claim 15, wherein said shelving unit further comprises a walled semi-enclosure having opposing side-walls, and a plurality of opposing horizontal slats spaced along and attached to the interior of said side-walls for supporting said adjustable-height shelf at a selectable height.

20. The work evaluation apparatus for assessing job related functions according to claim 19, wherein said pre-drilled holes are spaced along said pole at various heights and angles to prompt said patient to assemble and disassemble said fasteners in various body positions.

21. The work evaluation apparatus for assessing job related functions according to claim 15, wherein said simulated plumbing module includes a vertical panel attachable to an exterior wall of said main bench, a horizontal shelf attached to and extending outward from said vertical panel, and a plurality of plumbing components including a faucet mounted on said horizontal shelf, and a plurality of valves and pipes mounted beneath said horizontal shelf which can be worked with conventional plumber's tools.

22. The work evaluation apparatus for assessing job related functions according to claim 15, wherein said simulated electrical module includes a vertical panel attachable to an exterior wall of said main bench, and various electrical components mounted on said vertical panel which can be worked with conventional electrician's tools.

* * * * *